(12) United States Patent
Kinkade et al.

(10) Patent No.: US 7,973,194 B1
(45) Date of Patent: Jul. 5, 2011

(54) HIGH SOLVATING CYCLOHEXANE DICARBOXYLATE DIESTERS PLASTICIZERS

(75) Inventors: Nancy Ellen Kinkade, Kingsport, TN (US); Kim Steven Chamberlin, Kingsport, TN (US); David Justin Olsen, Kingsport, TN (US); Mark Stephen Holt, Huntersville, NC (US); Martin James Stimpson, Lockeridge (GB); Charles Everette Kelly, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/726,801

(22) Filed: Mar. 18, 2010

(51) Int. Cl.
C07C 69/74 (2006.01)
C08G 63/02 (2006.01)

(52) U.S. Cl. .................... 560/127; 528/272

(58) Field of Classification Search .............. None
See application file for complete search history.

(56) References Cited

U.S. PATENT DOCUMENTS

| | | | |
|---|---|---|---|
| 2,920,119 A | 1/1960 | Egbert et al. | |
| 2,930,806 A | 3/1960 | Joly et al. | |
| 3,006,928 A | 10/1961 | Allais et al. | |
| 3,428,668 A | 2/1969 | Huelsmann et al. | |
| T864,003 I4 | 7/1969 | Foster | |
| 4,284,540 A | 8/1981 | Iida et al. | |
| 4,457,924 A | 7/1984 | Jasys et al. | |
| 4,462,934 A | 7/1984 | Jasys | |
| 6,284,917 B1 | 9/2001 | Brunner et al. | |
| 6,509,312 B1 | 1/2003 | Giersch | |
| 7,208,545 B1 | 4/2007 | Brunner et al. | |
| 7,297,738 B2 | 11/2007 | Gosse et al. | |
| 7,413,813 B2 | 8/2008 | Gosse et al. | |
| 7,585,571 B2 | 9/2009 | Gosse et al. | |
| 2008/0004387 A1 | 1/2008 | Weiss et al. | |
| 2009/0291304 A1 | 11/2009 | Gosse et al. | |
| 2010/0113664 A1 | 5/2010 | Bradshaw et al. | |

FOREIGN PATENT DOCUMENTS

| | | |
|---|---|---|
| CS | 107197 | 4/1963 |
| DE | 29824628 | 11/2001 |
| EP | 0 083 484 | 7/1983 |
| EP | 0 307 935 | 3/1989 |
| GB | 817 735 | 8/1959 |
| GB | 817 736 | 8/1959 |
| GB | 963 911 | 7/1964 |
| GB | 1 047 259 | 11/1966 |
| JP | 34002316 | 4/1959 |
| JP | 57000159 | 1/1982 |
| JP | 02034841 | 2/1990 |
| JP | 02069443 | 3/1990 |
| JP | 02223541 | 9/1990 |

(Continued)

OTHER PUBLICATIONS

Database CAPLUS Chemical Abstracts Service, Columbus, Ohio, US; Database Accession No. 1988:429991, Abstract of Kawashima et al. JP 62257153.*

(Continued)

*Primary Examiner* — Karl J Puttlitz
(74) *Attorney, Agent, or Firm* — Brett L Nelson; Bernard J. Graves, Jr.

(57) ABSTRACT

Diesters of 1,4-cyclohexane dicarboxylate are surprisingly more efficient PVC plasticizers and fuse PVC faster and at a lower temperature than similar phthalates or terephthalate diesters. Hydrogenated orthophthalate diesters are slower fusing, i.e., require higher temperatures, than do the corresponding orthophthalate diesters.

10 Claims, 4 Drawing Sheets

FOREIGN PATENT DOCUMENTS

| | | |
|---|---|---|
| JP | 2001207002 | 7/2001 |
| KR | 2009038514 | 4/2009 |
| KR | 10-2010-0132253 | 12/2010 |
| KR | 10-2010-0132253 A | 12/2010 |
| WO | WO 99 32427 | 7/1999 |
| WO | WO 2009 116657 | 9/2009 |
| WO | WO 2010/044638 A2 | 4/2010 |

OTHER PUBLICATIONS

Database CAPLUS Chemical Abstracts Service, Columbus, Ohio, US; Database Accession No. 2000:897952, Abstract of Brunner et al., DE 19927978.*

Database CAPLUS Chemical Abstracts Service, Columbus, Ohio, US; Database Accession No. 1978:137856, Abstract of Hasegawa et al. JP 52121596.*

Abstracts Service, Columbus, Ohio, US; Database Accession No. 1991:111988, Abstract of Koden et al.: "Optically-active biphenyl ester derivatives, liquid-crystal compositions containing them, and ferroelectric liquid-crystal display devices", JP 02223541.*

Edelson-Averbukh, Marina; Etinger, Alexander; Mandelbaum, Asher. "Intramolecular benzyl-benzyl interactions in protonated benzyl diethers in the gas phase. Effects of internal hydrogen bonding"; Journal of the Chemical Society, Perkin Transactions 2: Physical Organic Chemistry (1999). (6), pp. 1095-1105.

Edelson-Averbukh, M.; Mandelbaum, A. "Chemistry and Stereochemistry of Benzyl-Benzyl Interactions in MH+ Ions of Dibenzyl Esters upon Chemical Ionization and Collision-induced Dissociation Conditions"; Journal of Mass Spectrometry (1997). vol. 32, pp. 515-524.

Edelson-Averbukh, Marina; Mandelbaum, Asher. "Gas-Phase intramolecular benzyl-benzyl interactions in protonated dibenzyl derivatives containing benzyl-oxygen, -sulfur and -nitrogen bonds"; Journal Chemical Society, Perkin Transactions 2 (2000). (5), pp. 989-996.

Tanka, Nobuo; Hosoya, Ken; Tachibana, Yuji; Araki; Mikio; Tanka, Kazuhiko; Kaji, Aritsune. "Selectivity of 2-(1-pyrenyl)ethylsilylated silica gel in the isomer separation of cyclohexane derivates"; Journal of Chromatographic Science (1989). 27(12), pp. 735-740.

Verbit, Lawrence; Tuggey, Robert L. "Effects of certain central groups on the liquid crystal properties of dicarboxylic esters"; Liquid Crystals and Ordered Fluids (Aug. 1973). vol. 2, pp. 307-314.

* cited by examiner

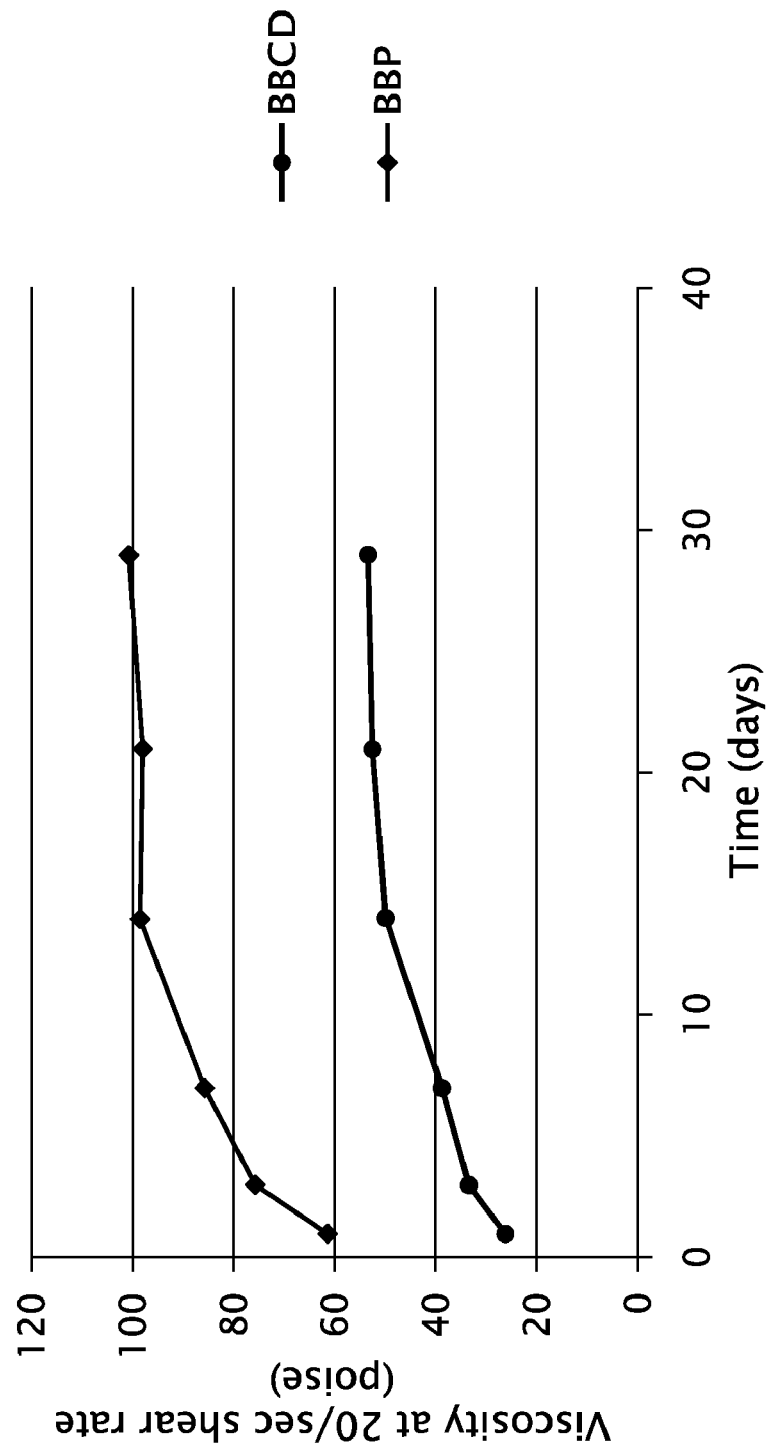

HIGH SOLVATING CYCLOHEXANE DICARBOXYLATE DIESTERS PLASTICIZERS

FIELD OF THE INVENTION

The present invention relates to high solvating plasticizers and compositions, such as polyvinylchloride (PVC) plastisols which including the plasticizers, as well as methods of making and using the plasticizers.

BACKGROUND OF THE INVENTION

There are a number of plasticizers used to produce flexible PVC and other flexible polymers worldwide. These differ in many respects, but all of them must possess certain characteristics. The plasticizer must be compatible with the polymer and make the polymer more flexible or softer. In PVC, the plasticizer also assists in the fusion of the PVC formulation to produce the final part; in this process the PVC resin particles dissolve/break apart, intermingle with all the other additives to produce the final homogenously dispersed part. Plasticizers that have a high affinity for PVC resin resulting in gelation and fusion at lower temperatures are called high solvating plasticizers. There are a number of chemical classes of high solvating plasticizers such as benzoates, butyl benzyl phthalate, di-isohexyl phthalate, and others.

Plasticized polymers are used in many different applications such as adhesives and sealants, coated fabrics, wire and cable coatings, foams, footwear, gaskets, inks, cosmetics, and medical. PVC based applications include floor coverings, wallpaper, roofing membranes, tubing, inks, toys, gloves, clothing, baby products, and calendared film. Polymers that have used plasticizers include PVC, polyurethanes, polyesters, cellulosics, polystyrene, polyvinyl alcohol, epoxies, rubbers, and polyamides.

SUMMARY OF THE INVENTION

An embodiment of the invention concerns a compound represented by the following structure:

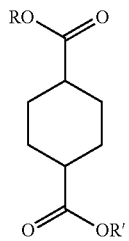

wherein R and R' are different and represent a $C_1$ to $C_{13}$ alkyl group, a $C_2$ to $C_{13}$ ether group, a cycloalkane group, or an aromatic group; and when both R and R' are an alkyl group the total number of carbons in both alkyl groups is less than 18.

Another embodiment concerns a composition comprising a compound as described in the preceding paragraph and at least one compound represented by the following structure:

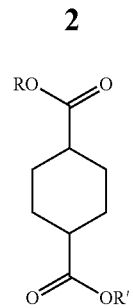

wherein R and R' are the same and represent a $C_1$ to $C_{13}$ alkyl group, a $C_2$ to $C_{13}$ ether group, a cycloalkane group, or an aromatic group.

Another embodiment concerns a plasticizer comprising a compound represented by the following structure:

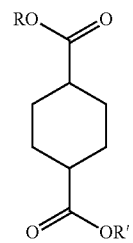

wherein R and R' are different and represent a $C_1$ to $C_{13}$ alkyl group, a $C_2$ to $C_{13}$ ether group, a cycloalkane group, or an aromatic group; and when both R and R' are an alkyl group the total number of carbons in both alkyl groups is less than 18.

Another embodiment concerns a plastisol comprising the plasticizer described in the preceding paragraph.

Still another embodiment concerns a method for producing a plasticizer representing by the following structure:

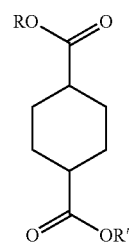

wherein R and R' are different and represent a $C_1$ to $C_{13}$ alkyl group, a $C_2$ to $C_{13}$ ether group, a cycloalkane group, or an aromatic group; and when both R and R' are an alkyl group the total number of carbons in both alkyl groups is less than 18, the method comprising: reacting a) 1,4-cyclohexane dicarboxylic acid or dimethyl cyclohexane-1,4-dicarboxylate and b) at least one alcohol in the presence of a catalyst to form the plasticizer.

Yet another embodiment concerns an article comprising a compound represented by the following structure:

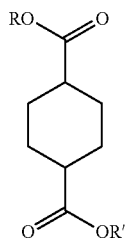

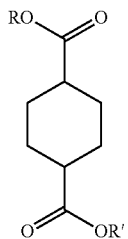

wherein R and R' are different and represent a $C_1$ to $C_{13}$ alkyl group, a $C_2$ to $C_{13}$ ether group, a cycloalkane group, or an aromatic group; and when both R and R' are an alkyl group the total number of carbons in both alkyl groups is less than 18.

BRIEF DESCRIPTION OF THE DRAWINGS

FIG. 4 shows the stabiltiy of the plastisol viscosity is the same for BBCD and BBP.

DETAILED DESCRIPTION

Figure 1:
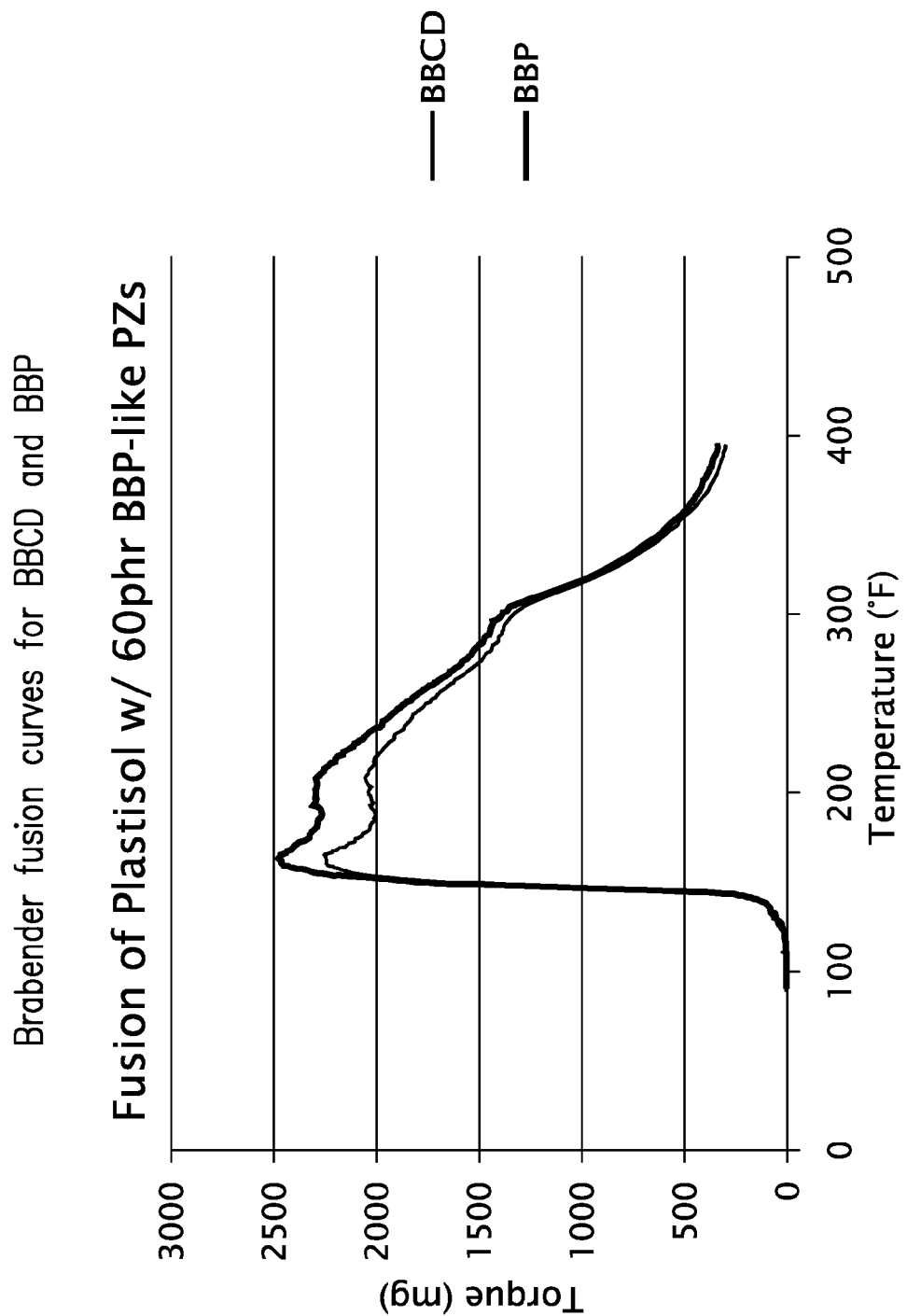
FIG. 1 shows Brabender fusion curves for BBCD and BBP.
Figure 2:
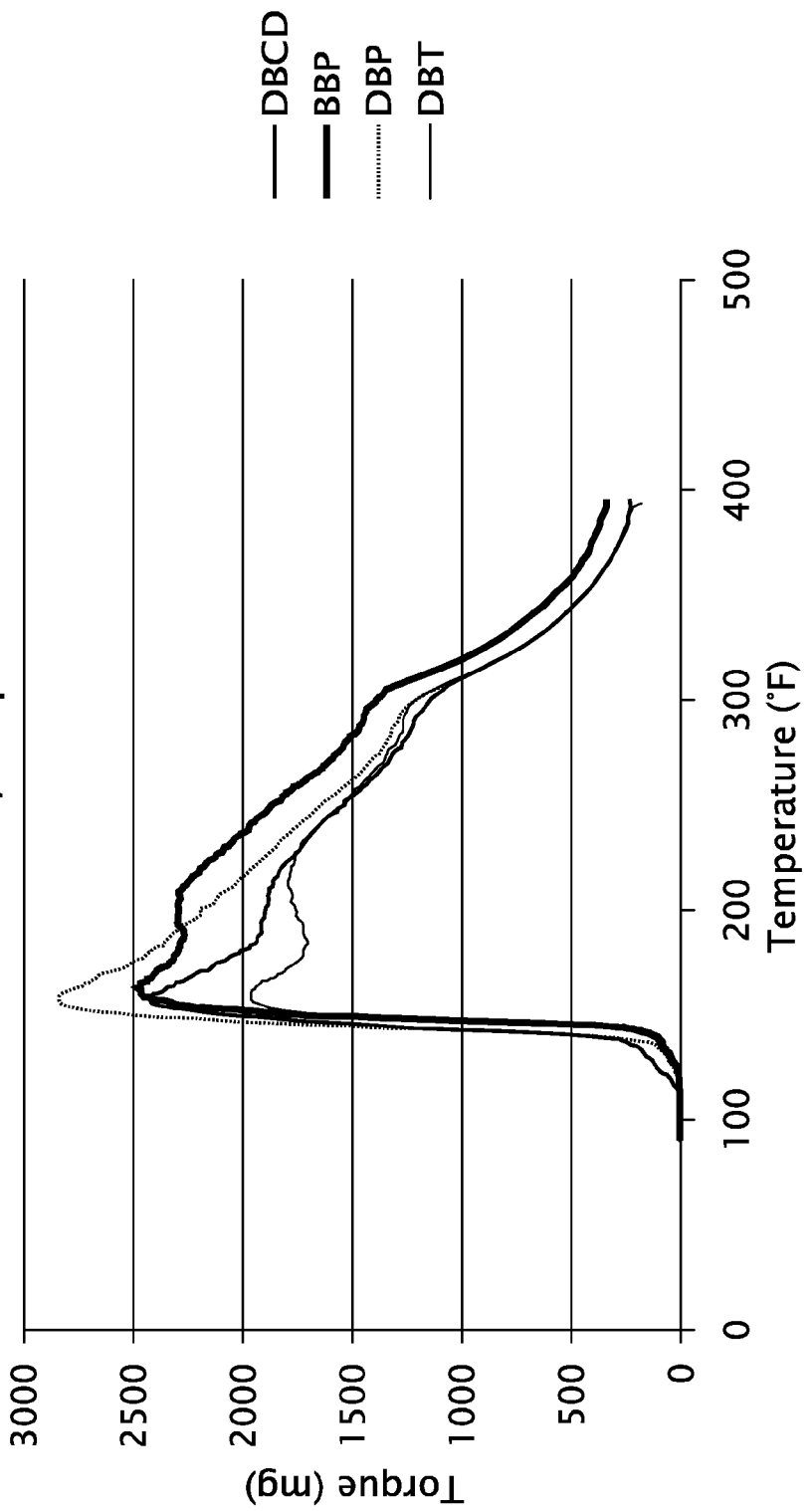
FIG. 2 shows Brabender fusion curves for DBCD, DBP, DBT and BBP.

This invention relates to compounds which are useful as high solvating plasticizers and compositions, such as polyvinylchloride (PVC) plastisols including the plasticizers, as well as methods of making and using the plasticizers and plastisols. The plasticizers fuse at lower temperatures than expected, gel at lower temperatures, and have lower than expected viscosity. These improved properties come while retaining plasticization efficiency based on Shore A hardness of the fused PVC.

Unless otherwise indicated, all numbers expressing quantities of ingredients, properties such as, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

In one embodiment, the plasticizers are represented by the following structure:

wherein R and R' are different and represent a straight chain or branched $C_1$ to $C_{13}$ alkyl group, a straight or branched $C_2$ to $C_{13}$ ether group, a cycloalkane group, or an aromatic group, and when both R and R' are an alkyl group the total number of carbons in both alkyl groups is less than 18.

According to an embodiment, the alkyl group can be straight or branched and could include methyl, ethyl, propyl, n-butyl, isobutyl, mixed pentyls, mixed hexyls, mixed heptyls, 2-ethylhexyl, mixed octyls, mixed nonyls, mixed decyls, mixed undecyls, mixed dodecyls, and mixed tridecyls. Examples of an ether group include diethylene glycol monobutyl ether, propylene glycol isobutyl ether, and dipropylene glycol monoethyl ether. Examples of cycloalkanes include cyclohexyl and methylcylcohexyl. Moreover, examples of useful aromatics include benzyl and tolyl.

In an embodiment, a plasticizer composition includes a 1,4-cyclohexane dicarboxylate diester. These compounds can be derived, for example, via an esterification reaction or a trans-esterification reaction. For example, the compounds may be derived from the reaction of 1,4-cyclohexane dicarboxylic acid; and mixtures of alcohols. The reaction can result in a mixture of diesters. For example, the reaction can result in a mixture of the cis and trans isomers of the mixed ester (i.e. where each ester is different) and the cis and trans isomers of the same esters. Moreover, suitable alcohols include straight chained or branched methanols, ethanols, propanols, butanols, pentanols, hexanols, heptanols, octanols, nonanols, decanols, undecanols, dodecanols, and tridecanols. The alcohols can also be aromatic or cyclic. Alternatively, the compounds may be derived from the reaction of dimethyl cyclohexane-1,4-dicarboxylate and a mixture of alcohols.

In one embodiment, the composition includes a mixture of 1,4-cyclohexane dicarboxylate molecules. For example, the composition could include a mixture of the cis and trans isomers of the mixed ester and the cis and trans isomers of the dibutyl and dibenzyl esters. For example, the composition can have mixtures of dibutyl 1,4-cyclohexane dicarboxylate (DBCD), dibenzyl 1,4-cylcohexane dicarboxylate (BZCD) and butyl benzyl 1,4-cyclohexane dicarboxylate (BBCD). Moreover, the various esters can be present in the mixture in various ratios. For example, the composition can include a mixture of from about 0 to about 80 weight % DBCD, from about 0 to about 50 weight % BZCD, and from about 20 to about 80 weight % BBCD or 10 to about 60 weight % DBCD, from about 10 to about 40 weight % BZCD, and from about 20 to about 60 weight % BBCD.

According to one embodiment, the compounds can be produced by contacting 1,4-cyclohexane dicarboxylic acid or dimethyl cyclohexane-1,4-dicarboxylate and at least one alcohol in the presence of a catalyst. The catalyst can be, for example, a Lewis Acid or Lewis base catalyst such as, for example, a titanate or potassium hydroxide. The catalyst can be present in an amount of from about 50 ppm to about 5000 ppm; from about 100 ppm to about 4000 ppm; or from about 200 ppm to about 3000 ppm. The reaction mixture can be run at a temperature of from about 65° C. to about 220° C., from about 140° C. to about 210° C. or from about 170° C. to about 200° C. Moreover, the reaction can be run at a pressure of from about 20 torr to about 800 torr, from about 500 torr to about 780 torr, or from about 700 torr to about 760 torr.

In one embodiment volatiles can be distilled at a vapor temperature of from about 65° C. to about 130° C. Moreover, after sampling for completion any excess alcohols can be remove at a temperature of from about 150° C. to about 220° C. and a pressure of from about 10 torr to about 100 torr.

Upon completion of the reaction, the reactor can be adjusted to atmospheric pressure and cooled to a temperature of from about 40° C. to about 100° C. or 40° C. to about 100° C. According to one embodiment, the completed reaction mixture can be washed up to three or more times with a wash solution, such as, for example, 2.5% NaOH in water, discarding the lower layer after each wash. The completed reaction mixture can also be washed up to three times or more with distilled or deionized water after which any residual water can be removed via, for example, a vacuum. Heat can be applied to the vacuum (up to about 150° C.) to facilitate water removal. Additional purification steps include carbon purification and filtration to remove the carbon.

For example, a plasticizer according to the present invention can be produced by charging 1 Mole of dimethyl cyclohexane-1,4-dicarboxylate to an excess of n-butyl alcohol (3-12 moles) along with 50-5000 ppm of a Lewis Acid or Lewis base catalyst (preferably a titanate or potassium hydroxide). This is heated while distilling volatiles at a vapor temperature of 65-115° C. Benzyl alcohol (2-4 moles) is added and heating is continued while distilling volatiles at a vapor temperature of 118-170° C. After sampling for completion, the excess alcohols are removed at 150° C. and 50 torr and the reactor is adjusted to atmospheric pressure. The reactor is then cooled to 85° C. and three 2.5% NaOH in water washes are added with the lower layer being discarded after each wash. Three washes with distilled or deionized water are then performed after which 50 torr vacuum is applied to the reactor and the reactor is heated to 150° C. to remove residual water. Carbon is added and the mixture is stirred one hour. The mixture is filtered through a filter aid to remove the carbon.

An embodiment according to the present concerns a plastisol which includes the high solvating plasticizers. Plastisols can be prepared using a high, low or combination intensity mixers, such as ribbon blenders, conical screw, planetary, Cowles, Morehouse, or any other suitable mixer. Ingredients used in making plastisols include PVC, acrylic or other polymeric resins; primary or secondary plasticizers; fillers; pigments; heat stabilizers; solvents; and other ingredients known in the industry. According to one embodiment, the plasticizers can be added to the plastisols at a range of from about 1.0 weight % to about 60 weight %, or at a range of from about 5.0 weight % to about 40 weight %, or even at a range of from about 10.0 weight % to about 30 weight % by weight depending on the efficiency of the plasticizer and the desired properties of the final product. The order of ingredients, shaft rpm, mixing times, and temperature all play a role to the producing a plastisol with reproducible quality. Typically plastisol temperature during mixing is maintained at less than 95° F. (35° C.), or even less than 80° F. (27° C.), though in some cases where for instance a higher viscosity is desired, the maximum temperature can be higher. Air is both incorporated in the mixing process and may also be introduced from the surface of the dry ingredients. If necessary, it can be removed by deaeration under reduced pressure either during or after mixing. Some of the air will be released if a plastisol is stored.

In one embodiment, the present plasticizers may be incorporated into vinyl chloride resin, along with or without other additions, by any suitable process such as, mixing or kneading of the ingredients. A desirable procedure involves forming a vinyl resin dispersion which can be cast in a film or thicker body, and then heated to form a homogeneous body of plasticized resin. Such dispersions are suspensions of vinyl chloride resin particles in nonaqueous liquids including the plasticizer which do not dissolve the resin at ordinary temperatures but do at elevated temperatures. If the liquid phase consists only of plasticizer, the dispersion is often termed as "plastisol," whereas if the dispersing liquid also contains volatile organic solvents or organic components which evaporate upon heating, the dispersion is often termed as "organosol." Both plastisols and organosols may include other additives, including stabilizers, normally used in vinyl chloride resin compositions. The term "plastisol" as used herein is intended to include both plastisols and organosols.

The plasticizers according to this invention may be added at any time and in any convenient manner to the PVC plastisol. If desired, the PVC plastisol and viscosity reducing compounds may be mixed simultaneously, for example, in conventional mixing or blending equipment.

The plasticizers according to this invention may be used to make numerous products. For example, the plasticizers can be used in adhesives and sealants, coated fabrics, wire and cable coatings, foams, footwear, gaskets, inks, cosmetics, and medical. PVC based applications include floor coverings, wallpaper, roofing membranes, tubing, inks, calendared film, Polymers that have used plasticizers include PVC, polyurethanes, polyesters, cellulosics, polystyrene, polyvinyl alcohol, epoxies, rubbers, and polyamides.

Products which employ the plasticizers of the present invention can be prepared or manufactured via numerous known processes. For example, the products or articles can be made or manufactured by hot or cold dipping, slush molding, or cavity molding; direct or reverse roll coating, knife coating or laminating adhesive; various spray processes or any other process known in the industry.

The following examples are submitted for a better understanding of the invention.

EXAMPLES

The formulation used in the examples detailed herein for a PVC plastisol is shown in Table 1. Plastisols were prepared using Geon™ 121A PVC resin (1 micron dispersion grade), Jenkinol™ epoxidized soybean oil (ESO) or Drapex 6.8 ESO and Akcrostab™ LT4798 heat and light stabilizer and the plasticizer of interest. The plastisols (60 parts per hundred (phr) plasticizer and 3 phr ESO and heat stabilizer) were prepared using a FlackTek DAC 150 SpeedMixer™ at 2000 rpm for two 45 sec intervals with a rest period in between such that the plastisol temperature did not exceed 35° C. (95° F.).

Plastisol fusion properties were determined on 60 ml of plastisol with an IntelliTorque Plasti-Corder™ 7150 Brabender™ torque rheometer with conical twin-screw roller blades co-rotating at 32 rpm and a 10° F./min (5.7° C./min) temperature ramp from 95 to 375° F. (35-195.5° C.) with 1 minute holds at the beginning and end. Table 2 contains Brabender data showing the results for a diisononyl orthophthalate (DINP) and the cyclohexane dicarboxylate analogue (DINCH). The orthophthalate fuses and gels at lower temperatures than the cyclohexane dicarboxylate analogue. Gel temperatures were calculated two ways. The first uses the temperature at which the tangent to the inflection point on the Brabender curve intersects with the baseline. The second gelation temperature method uses a temperature gradient bar and a method very similar to that documented in SPI-VPD method BE146, except that an 8 mil drawdown was used and allowed to sit for 10 minutes before applying the aluminum foil, rolling from the hot end to the cold end and then removing. The gel temperature with this method is the temperature of the bar just before where plastisol is observed on the foil.

Table 3 shows the unexpected results for the 1,4-cyclohexane dicarboxylate analogues of the butyl benzyl terephalate, butyl benzyl orthophthalate and dibutyl tere- and ortho-phthalates. Unlike the comparative example for the 1,2 cyclohexane dicarboxylate and orthophthalate, the 1,4-cyclohexane dicarboxylate and terephthalate examples show no difference in fusion or gel temperatures.

Figure 3:
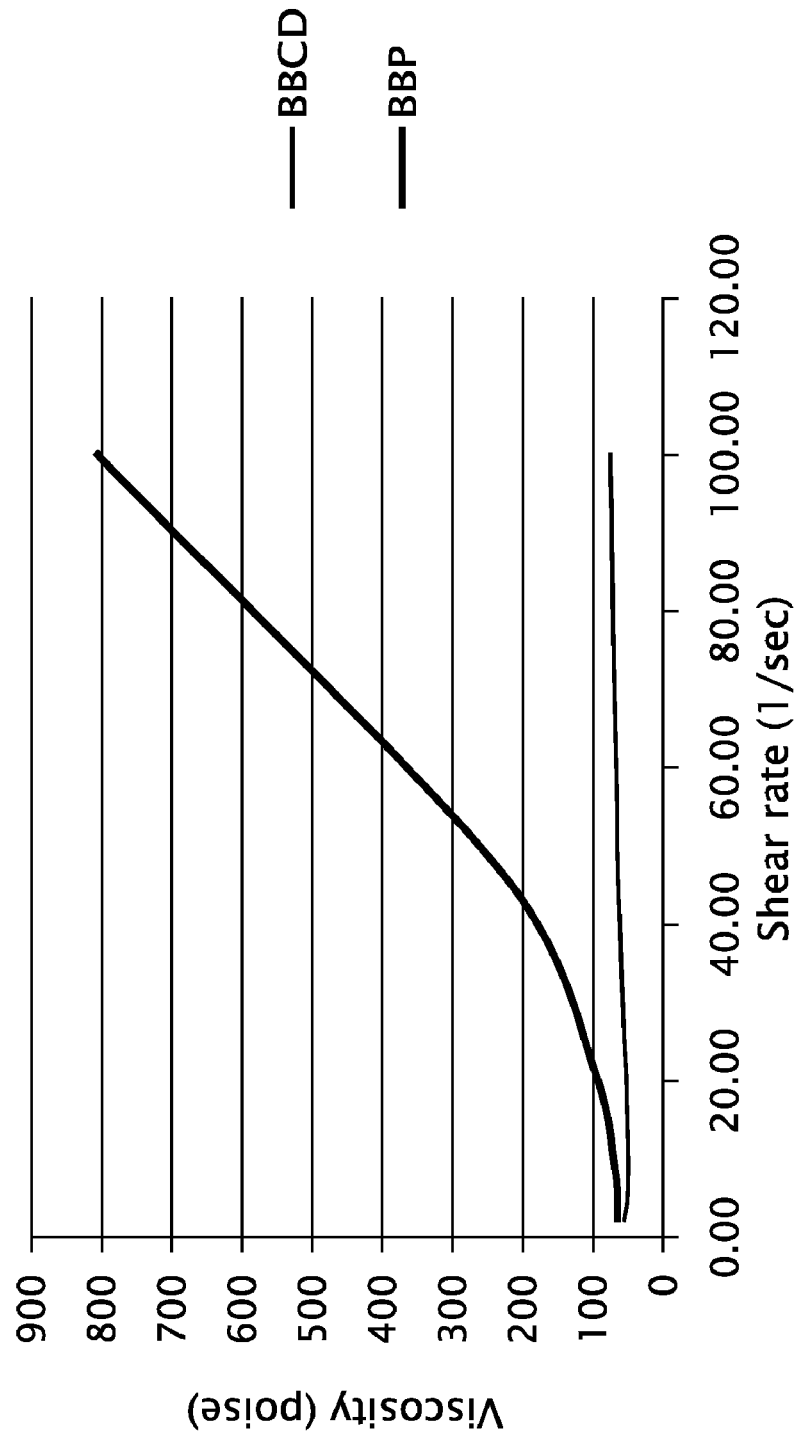
FIG. 3 shows the viscosity of BBCD is more stable as the shear rate is changed than BBP.

The viscosity of the plastisol containing the 1,4-cyclohexane dicarboxylate (CD) is lower and more stable with respect to increasing shear than that of the analogous orthophthalate. The viscosity of a BBP containing plastisol increases dramatically while that for the CD analogue is lower and quite stable with increasing shear rate as shown in FIG. 3. The stability with time for the two plastisols is the same and shown in FIG. 4.

The viscosity of the CD plasticizer is lower than for the analogous orthophthalate. For instance, BBCD and BBP have viscosities of 3000 and 4300 cP, respectively at shear rates of 10-100/sec. In addition the BBCD containing plastisol is readily deaerated while the analogous one containing BBP is very difficult to deaerate due to the stability of the bubbles.

The hardness of PVC is a measure of the efficiency of the plasticizer. For equal amounts of plasticizer, a softer PVC indicates it contains a more efficient plasticizer. Shore A hardness of 67 was measured for both a 60 phr BBCD PVC and a 60 phr BBP PVC.

TABLE 1

Formulation for plastisol examples.

| Component | Conc. (PHR) |
| --- | --- |
| Geon 121A | 100 |
| Plasticizer | 60 |
| Akrostab LT 4798 | 3 |
| Jenkinol or Drapex 6.8 | 3 |
| ESO | |

TABLE 2

Di-isononyl 1,2 cyclohexane dicarboxylate fuses and gels at higher temperatures than di-isononyl orthophthalate.

| | DINCH | DINP |
| --- | --- | --- |
| Fusion Time (m:s) | 20.66 | 17.83 |
| Fusion Temperature (C.) | 154 | 143 |
| Gelation Speed (mg/min) | 291 | 300 |
| Inflection Point (m:s) | 17.70 | 14.87 |
| Inflection Temp (C.) | 131 | 115 |
| Gradient plate gel temperature (C.) | 109 | 73 |

TABLE 3

Butyl benzyl 1,4-cyclohexane dicarboxylate (BBCD) fuses and gels at the same temperatures as butyl benzyl orthophthalate (BBP) and dibutyl 1,4-cyclohexane dicarboxylate (DBCD) fuses and gels at the same temperatures as dibutyl phthalate (DBP) or dibutyl terephthalate (DBT).

| | BBCD | BBP | DBCD | DBP | DBT |
| --- | --- | --- | --- | --- | --- |
| Fusion Time (minutes) 1st peak | 7.60 | 7.47 | 6.77 | 7.33 | 7.43 |
| Fusion Temperature (C.) 1st peak | 73 | 72 | 69 | 71 | 71 |
| Fusion time (minutes) 2nd peak | 10.03 | 9.30 | 10.50 | na | 10.63 |
| Fusion Temperature (C.) 2nd peak | 98 | 93 | 98 | na | 101 |
| Inflection Point (minutes) | 7.03 | 6.90 | 6.73 | 7.00 | 6.97 |
| Inflection Temp (C.) | 64 | 64 | 62 | 63 | 64 |
| Gel Temp (tangent) (C.) | 61 | 61 | 59 | 57 | 60 |
| Gradient plate gel temperature (C.) | 56 | 51 | 51 | 51 | 54 |

The invention has been described in detail with particular reference to certain exemplary embodiments thereof, but it will be understood that variations and modifications can be effected within the spirit and scope of the invention.

We claim:
1. A compound represented by the following structure:

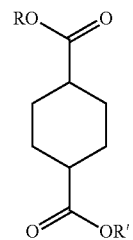

wherein R and R' are different and represent a butyl group or a benzyl group wherein said butyl group is an isobutyl group or an n-butyl group.

2. A composition comprising a compound according to claim 1.

3. A composition, comprising from about 10 to about 50 weight % dibutyl 1,4-cyclohexane dicarboxylate, from about 30 to about 60% dibenzyl 1,4-cylcohexane dicarboxylate, and from about 20 to about 60 weight % butyl benzyl 1,4-cyclohexane dicarboxylate.

4. A plasticizer comprising the compound according to claim 1.

5. A plastisol comprising the plasticizer according to claim 4.

6. A method for producing a plasticizer representing by the following structure:

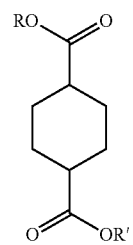

wherein R and R' are different and represent a butyl or a benzyl wherein said butyl is an isobutyl group or an n-butyl group;

the method comprising:

reacting a) 1,4-cyclohexane dicarboxylic acid or dimethyl cyclohexane-1,4-dicarboxylate and b) at least one alcohol in the presence of a catalyst to form the plasticizer.

7. An article comprising the compound according to claim 1.

8. The article according to claim 7, wherein the article is an adhesive, a sealant, a coated fabric, a wire coating, a cable coating, a foam, footwear, a gasket, an ink, a cosmetic, or a medical device.

9. The article according to claim 7, wherein the article is a floor covering, wallpaper, a roofing membrane, a tubing, or a film.

10. The article according to claim 7, wherein the article is produced via hot dipping, cold dipping, slush molding, cavity molding, direct roll coating, reverse roll coating, knife coating, laminating adhesive, spraying or a combination thereof.

* * * * *